United States Patent [19]

Jacobson

[11] Patent Number: 5,366,435

[45] Date of Patent: * Nov. 22, 1994

[54] THERAPEUTIC TREATMENT OF MAMMALS

[76] Inventor: Jerry I. Jacobson, 153 Raintree Trail, Jupiter, Fla. 33458

[*] Notice: The portion of the term of this patent subsequent to Dec. 14, 2010 has been disclaimed.

[21] Appl. No.: 166,687

[22] Filed: Dec. 14, 1993

Related U.S. Application Data

[63] Continuation of Ser. No. 973,230, Nov. 6, 1992, Pat. No. 5,269,746, which is a continuation-in-part of Ser. No. 172,388, Mar. 24, 1988, abandoned, which is a continuation-in-part of Ser. No. 840,881, Mar. 16, 1986, abandoned, which is a continuation-in-part of Ser. No. 451,021, Dec. 20, 1982, abandoned.

[51] Int. Cl.$^5$ .............................................. A61N 1/00
[52] U.S. Cl. ...................................................... 600/13
[58] Field of Search .................. 128/653.1; 600/9, 13, 600/14

[56] References Cited

U.S. PATENT DOCUMENTS

| | | | |
|---|---|---|---|
| 781,448 | 1/1905 | McIntyre | 600/13 |
| 2,099,511 | 1/1934 | Caesar | 331/106 |
| 2,103,440 | 12/1937 | Weissenberg | 600/9 |
| 3,738,369 | 6/1973 | Adams et al. | 607/17 |
| 3,890,953 | 6/1975 | Kraus et al. | 600/14 |
| 4,323,056 | 4/1982 | Borrelli et al. | 600/10 |
| 4,576,172 | 3/1986 | Bentall | 607/71 |
| 4,611,599 | 9/1986 | Bentall et al. | 607/27 |
| 5,269,746 | 12/1993 | Jacobson | 600/13 |

OTHER PUBLICATIONS

Dixey, R. & Rein, G. (1982) "H-noradrenaline Release Potentiated in a Clonal Nerve Cell Line by Low Intensity Pulsed Magnetic Fields", Nature, 296, 253–256.

Cremer-Bartels, G., Krause, K. & Kuechle, J. J. (1983), "Influence of Low Magnetic Field-Strength Variations on the Retina and Pineal Gland of Quails and Humans", *Graefe's Archives of Clinical and Experimental Ophthalmology*, 220, 248–252.

Reuss, S., Semm, P. & Vollrath, L. (1983), "Different Types of Magnetically Sensitive Cells in the Rat Pineal Gland", *Neuroscience Letters*, 40, 23–26.

Welker, H. A., Semm, P., Willig, R. P., Commentz, J. C., Wiltsehko, W. & Vollrath, L. (1983), "Effects of an Artificial Magnetic Field on Serotonin N-acetyltransferase Activity and Melatonin Content of the Rat Pineal Gland", *Experimental Brain Research*, 50, 426–432.

Bliss, V. L. & Heppner, F. H., (1976), "Circadian Activity Rythms Influenced by Near Zero Magnetic Field", *Nature*, 261, 411–412.

DeLorge, J. (1979), *Effects of Magnetic Fields on Behavior in Nonhuman Primates*, In T. Tenforde (Ed.), "Magnetic Field Effects in Biological Systems", (p. 32), New York: Plenum Press.

Adey, W. R. (1981) "Tissue Interactions with Nonionizing Electromagnetic Fields", *Physiological Review*, 61, 435–514.

Sandyk, R. "Magnetic Fields in the Therapy of Parkinsonism", Int'l Jrnl of Neuroscience, 1992, vol. 66, pp. 209–235.

Sandyk, R. "Successful Treatment of MS with Magnetic Fields", Int'l Jrnl of Neuroscience, 1992, vol. 66, pp. 237–250.

Anninos, P. A. et al, "Mag. Stimulation in the Treatment of Partial Seizures", Int'l Jrnl of Neuroscience, 1991, vol. 60, pp. 141–171.

Sandyk, R. "Resolution of Longstanding Symptoms of MS by Application of Picotesla Range Magnetic Fields" Intnl Jrnl Neuroscience, 1993, vol. 70, pp. 255–269.

Sandyk, R. "Magnetic Fields Normalize visual Evoked Potentials and Brainstem Auditory Evoked Potentials in MS", Intnl Jrnl Neuroscience, 1993.

Sandyk, R. "Successful Treatment of an Acute Axacerbation of MS by External Magnetic Fields", Internal Jrnl of Neuroscience, 1993.

*Primary Examiner*—Francis Jaworski
*Attorney, Agent, or Firm*—Quarles & Brady

[57] ABSTRACT

A method of therapeutically treating various virus and genetically based diseases comprises subjecting mammals suffering from said diseases to an alternating magnetic field having flux density and a frequency calculated as a function of the mass of the oncogene, target gene, messenger RNA, protein, enzyme and/or hormone. The calculation is such to equate the energy of a current electromagnetically induced in the mammal with the gravitational energy of the target genetic material, such that a dual resonance is achieved.

12 Claims, 1 Drawing Sheet

THERAPEUTIC TREATMENT OF MAMMALS

CROSS REFERENCE TO RELATED APPLICATIONS

This application is a continuation of application Ser. No. 07/973,230 filed Nov. 6, 1992, now U.S. Pat. No. 5,269,746, which is a continuation-in-part of my co-pending application Ser. No. 172,388, filed Mar. 24, 1988, now abandoned which is a continuation-in-part of application Ser. No. 840,881, filed Mar. 16, 1986 which in turn is a continuation-in-part of prior filed application Ser. No. 451,021, filed Dec. 20, 1982. Ser. No. 840,881 and Ser. No. 451,021 are now abandoned.

BACKGROUND OF THE INVENTION

This invention relates to applying electromagnetic energy to living tissues for therapeutic purposes, and in particular to applying a specific magnetic flux density and frequency of electromagnetic radiation calculated from the mass of targeted tissues, to achieve a healthful response in said tissue, apart from other influences thereon.

PRIOR ART

In the past, a number of procedures have been described to be useful in the treatment of various diseases which involved the employment of magnetic fields to accomplish their objectives. In U.S. Pat. No. 4,323,056 there are disclosed numerous prior art patents and publications which describe the use of electromagnetic materials and electro-magnetic fields, e.g., lasers, microwaves and radio frequency (RF) induced magnetic fields, in the therapeutic treatment of mammals suffering from various disease conditions. These patents and publications typically teach ingestion of magnetic materials, for example, iron oxide, in patients in conjunction with the application of a magnetic force. Ferromagnetic particles become heated as a result of the coupling thereof to the magnetic field through their dielectric and hysteresis loss, the induced heating constituting the therapeutic properties of this form of treatment.

These prior art processes were not therapeutically successful for a number of reasons. The magnetic form of iron oxide is insoluble in body fluids and in substantial concentrations may be toxic to or rejected by the body. In addition, in many instances the amount of heat generated by these particles was excessive and substantial unwanted injury to tissue was experienced.

Devices for applying electromagnetic energy to living tissue are also disclosed, for example, in U.S. Pat. Nos. 2,099,511-Caesar; 2,103,440-Weissenberg; and 781,448-McIntyre. Caesar teaches applying an alternating magnetic field to a localized area, and it is also believed to rely primarily on localized heating (diathermy). Weissenberg teaches application of a low level field and McIntyre teaches means ostensibly applying a homogeneous field to the whole body of a plant or animal, for therapeutic reasons. These patents demonstrate the interest in application of electromagnetic energy to plants and animals for therapeutic reasons, but do not teach any particular means for determining a field strength or frequency that will have any particular beneficial effects.

In connection with accelerating healing of traumatic injuries, U.S. Pat. Nos. 4,611,599 and 4,576,172, both to Bentall, and 3,890,953-Kraus et al and 3,738,369-Adams et al, induce particular fields for purposes of promoting growth of damaged tissue. The prior art includes a wide range of field strengths and frequencies, Bentall teaching RF frequencies and Kraus teaching power line frequencies.

Of course, with variations in power level from diathermy to the microwatt levels of the Bentall patent, and frequencies which vary over similar orders of magnitude, there is nothing in the prior art that provides any rationale or means for calculating particular magnetic flux densities and alternating polarity field frequencies that will have any particular effect specific to defined elements of the plant or animal. According to the present invention, a means are provided for calculating precisely the energies and frequencies appropriate for inducing in the plant or animal a stable and healthful response, by tailoring the flux density and frequency to specific targets, e.g., gene elements. A homogeneous field is applied at a level calculated so as to equate the energy of a current induced in the plant or animal with the characteristic gravitational energy of a target element of said plant or animal, due to the mass of said element. As will be seen herein, it is possible to directly mathematically correlate a field calculated according to the present method with fields which are emitted during normal physiological functions such as heartbeat and brain waves. The result is a low level magnetic field, as little as $10^{-8}$ gauss. The frequency of alternation is very low, even approaching a direct current field. The result is a beneficial impetus on the target elements to maintain or resume their nominal healthy functioning.

The invention, including tailoring target-specific radiation for effect on specific masses of biological elements and for achieving homeostasis (a stable healthy condition) therein, provides a method for therapeutically treating patients suffering from various disease conditions. In each case the applied magnetic forces are specific to the mass of the elements to be affected. The invention uses low level mass-characteristic fields and thus avoids disadvantages of prior art methods, characterized by high power, high frequency, and levels not related to the target masses. By accomodating variations in target element mass, the invention involves therapeutically treating patients suffering from numerous disease conditions. Over an extended period of time, the patient is subjected to a magnetic field having a flux density of from about $6 \times 10^{-6}$ gauss to about $6 \times 10^{-10}$ gauss. This level is of course lower than ambient fields due to the earth's magnetic poles, but the effect of the calculated field, being tuned specifically to a target mass, nevertheless achieves a positive effect. Even more particularly, patients suffering from various disease conditions may be therapeutically treated according to the invention by subjecting said patients to a magnetic aligned perpendicularly to the longitudinal axis of the patient over an extended period of time. Said magnetic field possessing a magnetic flux density of from about $6 \times 10^{-10}$ to $6 \times 10^{-6}$ gauss.

In the most satisfactory embodiment of this invention, patients suffering from various disease conditions may be successfully treated. By basing the applied field strength on specific calculated mass, disease conditions are treatable across a broad range of viral etiology, or more particularly those of an oncogenic or light chain polypeptide, infectious RNA or DNA etiology. With appropriate accuracy virally and genetically induced diseases such as epilepsy, certain glaucomas, certain deafness, palsy, certain diabetes, rheumatoid arthritis, neuralgias, certain retinopathies, nerve tics, Parkinsons's disease, certain anemias such as sickle cell anemia, and other like diseases are all subject to arrest or reversal. The patients suffering from these disease conditions and which may be satisfactorily treated by the practice of the instant invention are mammals, including both human beings and other animals who suffer from such disease conditions. The listed diseases are suggestions and the practioner of the instant invention will be able to determine patients and disease conditions which may be satisfactorily therapeutically treated by practicing the process of the invention.

Usually, a whole virus is 100 times greater in mass than the nucleic acids which are infectious to homo sapiens. Whole viruses may infect animals, inducing carcinoma, sarcoma and variations of these diseases involving other tissues, such as, muscle, or nerves. Oncogenic nucleic acids of infectious viral origin, which are 10 to 10,000 times smaller in mass, may infect man inducing at least some of the aforementioned disease conditions. These viruses and nucleic acids are apt target elements.

The process of the instant invention requires that the patient sought to be treated thereby must be subjected to the effects of a magnetic field over an extended period of time. More particularly, the patient to be treated must be subjected to the effects of a magnetic field having a magnetic force or magnetic flux density calculated according to a formula discussed herein, the flux density being of from about $6 \times 10^{-6}$ gauss to about $6 \times 10^{-10}$ gauss. The frequency can be from a high sufficient to yield a wave form of about $10^{-6}$ centimeters, which is in the ultraviolet range and corresponds to viral length, to a low frequency mass-dependent resonance according to a further formula discussed herein. Even more particularly, the magnetic field to which the human patient is to be exposed should be one which is sufficient to impart a magnetic field intensity to the patient of from about 0.12 to 126 oersteds, to about $6 \times 10^{-10}$ oersteds in air and preferably for human beings, from about $6 \times 10^{-8}$ oersteds in air to about $6 \times 10^{-10}$ oersteds in water which may be obtained with an alternating magnetic flux polarity density of from about $6.67 \times 10^{-11}$ teslas (MKS) to about $6.67 \times 10^{-12}$ teslas (MKS) and about $6 \times 10^{-8}$ gauss, in air and H$_2$O (CGS) with the imparting of from about 0.1 to 1.5 (MKS) to about $10^{-6}$ to $10^{-7}$ (CGS) amperes, and having a frequency of magnetic flux sufficient to yield a magnetic wave form of $10^{-6}$ centimeters. The magnetic force and field which are calculated for application according the instant invention may be generated in a manner known to the worker skilled In the art to obtain the desired levels of energy to which the patient is to be exposed. Preferably, the magnetic field to be employed in the practice of this invention may be obtained through the employment of a solenoid device which is designed and driven with the required current to provide a magnetic field having the magnetic flux density to which the patient is to be exposed. The solenoid may be cylindrical in nature with a hollow core. The cylindrical solenoid is comprised of a multitude of turnings of thin metal electrically conductive wire. The solenoid which is employable herein can have, from the center of the wire to the center of the solenoid, a radius of about 2 meters and a length of from about 1.0 meters (CGS) with H$_2$O correction to about 10.0 meters (MKS) in air or larger, and preferably from about 2 meters to about 6 meters. The frame of the solenoid may be cork or styrofoam which have specific gravities of less than 1.0, the specific gravity of water. Although the size of the radius of the solenoid should be about 2 meters, when the patient being treated is a human being, it may be varied, but should be of sufficient size to accept the patient being treated, in all respects, including longitudinally, so as to expose the cross sectional aspect of the patient to the magnetic flux. The conductor of the solenoid occupies a plane parallel to the longitudinal axis of the patient and at a right angle to the magnetic lines of flux.

The solenoid employed in the practice of this invention may be constructed by creating a coil comprised of numerous turnings of the electrically conductive metal wire employed for such purpose. Preferably, the electrically conductive metal wire should be relatively thin so that sufficient turns thereof may be practically made to provide the necessary electromagnetic field when electrical power is introduced thereto. Copper wire for the MKS system as a relative maximum for non-human animals and germanium wire for the CGS and MKS systems, as well as steel, iron, tungsten and manganese, provide satisfactory results, while thin, nickel chrome wire, generally referred to as "nichrome" wire and silicon have provided most beneficial results in the practice of this invention. The electrically-conductive wire which may be employed in the constructions of the solenoid may have a diameter of from about 1 mil. to 1000 mils., although wire of other thickness may also be employed. In the most preferable embodiment of this invention germanium wire is employed in the treatment of humans. The number of turnings which will be required to construct the solenoid will be dictated by the electromagnetic force and magnetic flux density which is desired to be generated by the solenoid when powered by the electrical current to be employed.

In the practice of this invention, satisfactory results are obtained on humans, when an electrical current of about 0.1 to about 7.5 volts, (CGS) and preferably from about 0.1 to about 0.75 volts, (CGS, Ur corrected) has been applied to the solenoid to yield an electromagnetic field having a magnetic flux density of from about $6 \times 10^{-11}$ ksla (MKS), or about $6 \times 10^{-8}$ gauss with a frequency of magnetic flux density sufficient to yield a wave resonant at the level of the target particles, about $10^{-6}$ centimeters in length, and/or resonant due to equating their characteristic gravitational or inertial energy with the energy of a current to be induced therein. For animals of lower evolutionary scale, the intensity (H) may be increased, usually by a factor of about a hundred. While these ranges provide satisfactory results in the practice of the instant invention, other ranges may also be employed to provide satisfactory results. Disease etiology, size of the mammal, etc. will determine the field intensity (H) which then determines voltage; amperage, number of turns (N) and dimensions of solenoid.

In order to treat the patients suffering from the various disease conditions which may be treated by the instant invention, the necessary electrical power is applied to the solenoid to create the required electromagnetic field and magnetic flux density within the core thereof, so as to create a field having an intensity (H) of about 0.67 oersteds (MKS) to $7.6 \times 10^{-2}$ oersteds to about $7.6 \times 10^{-9}$ oersteds (CGS), to $6 \times 10^{-8}$ oersteds (MKS). For non-human mammals it may be from $6 \times 10^{-7}$ to $6 \times 10^{-5}$ oersteds (CGS). Prior to the application of the electrical power thereto, the patient is introduced and placed within the core of the solenoid, or at least that portion of the patient's body to be treated is so placed. After the electrical power, i.e., 0.1 to 7.5 volts, is applied to the solenoid, the patient is held within the core and within the two generated electromagnetic field for at least 20 minutes at a time before the electrical power is terminated and the patient removed. The patient may be held within the generated magnetic field for extended periods, up to an hour or more, while still obtaining the desired therapeutic results. In addition, the treatment procedure may be repeated as frequently as deemed necessary to obtain the desired therapeutic results. The length of time of each treatment, and the number of treatments which may be necessary will vary for each patient and each disease condition sought to be treated and these treatment conditions may be determined by the skilled worker for each patient and the condition being treated, as determined by the mass etiology of the disease condition, the atomic mass unit of the quantum etiological factor.

BRIEF DESCRIPTION OF THE DRAWINGS

Referring now to the drawings included within this Application, FIG. 1 shows a top view of the apparatus of this invention while

DETAILED DESCRIPTION OF THE PREFERRED EMBODIMENTS

Figure 1:
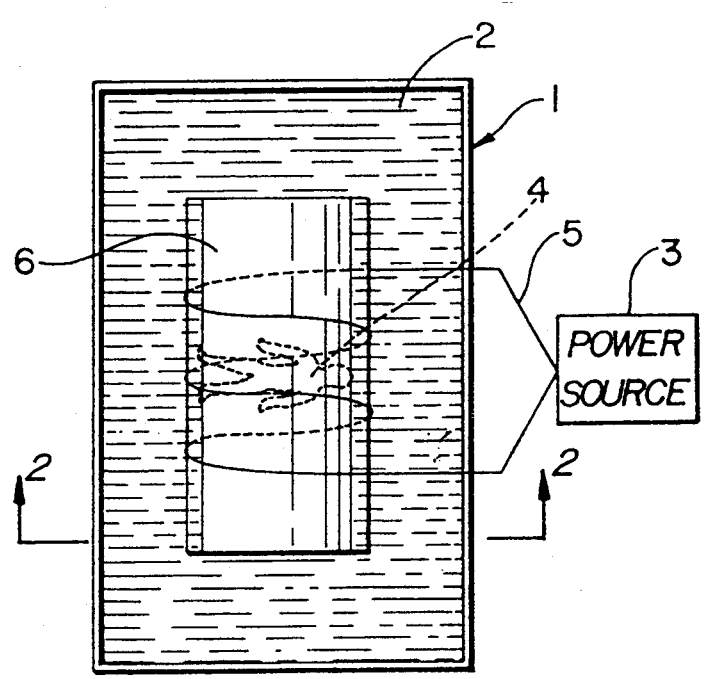
Figure 2:
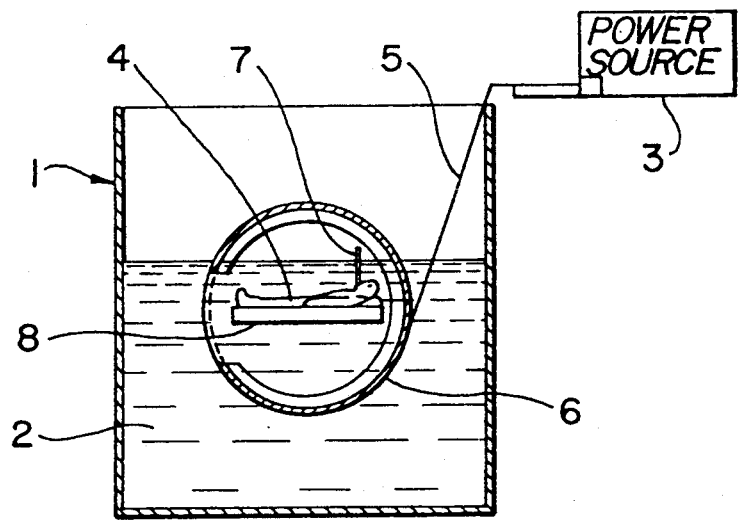
FIG. 2 shows a cross section thereof along line AA.

Water medium 2, within which the patient 4 is immersed is held in a tank 1 of sufficient size to hold the solenoid 6. The solenoid 6 is comprised of a column created by the continuous turns of the electrical conductive wire 5 the respective ends of which are connected to the electrical power source 3. When the power is turned on an electromagnet is created which generates the magnetic field to which the patient is exposed and which is required for the satisfactory practice of the instant invention.

In addition to the foregoing, it should be understood that the practice of the instant invention also envisions the use of electromagnetic fields generated by smaller solenoids where localized treatment of various specific parts or sections of the body are sought to be treated, rather than subjecting the entire body to the treatment contemplated by the practice of this invention. Thus, it is possible to treat a localized portion of the body, for example, the midsection of the torso, by employing a smaller solenoid having a width of 1-2 feet and diameter of 2-2_ feet into which the pertinent portion of the patient's body is placed in a water medium and employing the appropriate electrical energy to obtain the desired magnetic flux field to obtain the desired results. Likewise, the skilled worker may be able to employ various smaller sized solenoids to obtain the desired results upon the treatment of patients' knees and elbows only. It is also possible to induce the required field by applying a current rather than a magnetic field, i.e., to apply the same current level as induced by the solenoid. The invention may be illustrated by the following Examples:

EXAMPLE 1

A solenoid comprised of 40 turns of germanium wire (55 ohms/cm) is prepared. The interior core of the solenoid has a radius of 1.5 meters and the length is about 6.15 meters. The solenoid is placed in a waterproof bathtub 18 meters in length, 9 meters in width and 9 meters in depth, so as to manufacture clearance for magnetic flux, and immersed in water to a level reaching two-thirds of the diameter of the inner core of the solenoid. A styrofoam body holder into which the patient suffering from multiple myeloma is placed in a prone position at right angles to the length of the solenoid within the inner core of the solenoid so that the patient's head and feet are at opposite ends thereof. A direct electrical current of about 0.2 volts is applied to the solenoid thereby creating an electromagnetic field within the inner core of the solenoid having a magnetic field intensity (H) of about $6.5 \times 10^{-9}$ oersteds approximating the electrostatic constant and the patient is held therein exposed to this negative magnetic field for a period of twenty minutes, at which time the electrical current is withdrawn. Current (I) is about $10^{-7}$ amps and B is about $6.67 \times 10^{-8}$ gauss. After one hour the foregoing procedure is repeated and the entire process repeated once each hour for the next succeeding six hour period. At the end of this treatment period noticeable improvement in the patient is noted after the patient is removed from the solenoid.

EXAMPLE 2

The procedure of Example 1 is followed except that I is about $10^{-6}$ amperes and there is no water used, the patient being treated in air, the length of the solenoid is 6 meters and the voltage applied is about 2.0 volts, with like results being obtainable, an H equal to about $6 \times 10^{-8}$ oersteds. AC may also be employed wherein alternating polarity fields are most efficacious. Hysteresis may result in the break-up of intermolecular dipoles, which may be indicated in certain cases where large tumors are obstructive and cannot be surgically removed.

EXAMPLE 3

The procedure of Example 1 is followed except that 30 turns of germanium wire (55 ohms/cm.) are employed to form the solenoid, 5.9 meters in length and the voltage applied is from 1.5 to 0.15 volt, I may be about $10^{-6}$ amperes to $10^{-7}$ amperes, depending upon the etiology of the mass. The field intensity (H) is from about $6 \times 10^{-8}$ to $6 \times 10^{-9}$ oersteds. B is from about $6 \times 10^{-11}$ to $6 \times 10^{-12}$ teslas based upon the general formula equating inertial/gravtational energy ($e = mc^2$) with the energy of a unit of charge defining a current due to movement through space ($EI = energy = Bvl$), $mc^2 = Bvl$.

EXAMPLE 4

The procedure of Example 1 is followed except that 20 turns of germanium wire is employed to form a solenoid 3 meters in length and about 10 volts are applied thereto. (CGS, $u_r H_2O$ corrected). I may be about $10^{-5}$ amperes; H about $6 \times 10^{-7}$ oersteds and B is about $6 \times 10^{-6}$ gauss.

EXAMPLE 5

The desired flux density ("B") of the treatment procedure of the instant invention may also be determined by the formula $mc^2 = BvL$ coulomb, which sets in dual resonance gravitational potential and electromagnetic interaction potential. The desired flux density ("B") is established by having m = mass of the quantum genetic character (e.g. virus, oncogene, m-RNA, etc.); c = velocity of light; v = orbital velocity of the earth; and l = the height of the patient. (Coulomb = unity). Thus a sample equation is:

$$4\times10^{-20} \text{ g.} \times c^2 = B \times 3 \times 10^6 \text{ cm/sec} \times 2 \times 10^2 \text{ cm}$$

(wherein $c = 3 \times 10^{10}$ cm/sec) $B = 6 \times 10^{-8}$ gauss.

The foregoing magnetic flux density is small, substantially less than the magnetic field produced by the earth. However, the magnetic field at the calculated level is comparable to the heart's magnetic field, approximately $5 \times 10^{-7}$ gauss at approximately 72 beats per minute. Similarly, the strength is comparable to the magnetic fie emitted by the brain alpha rhythm in normal functioning, measured at about $10^{-9}$ gauss by the SQUID. Therefore, by comparing the gravitational energy ($E = mc^2$) with the energy per unit charge of a current (EMF "$E$" = Bvl), the resulting field is comparable to the biologically produced field during healthy physiologic functioning. Therefore, the invention is based upon the vibrational energy of the length of the human ("l") induced by electromagnetic oscillation producing mechanical vibrations, in dual resonance with the particular quantum systems of particles of mass "m". As a result, the particles vibrate in tune with the propagating magnetic field. The inertial velocity of the human subject, namely the orbital velocity of the earth, applies on the electromagnetic energy side of the equation ($E = $ Bvl coulomb). The velocity of the propogating wave (i.e., the velocity of "B" is the speed of light, "c").

It is a well known characteristic of electric force that the force between any two charges is cumulative with forces produced by other charges. According to so-called "gauge" theory, you could theoretically charge a whole laboratory up to a high voltage and any measurements taken of the force between two electrons within this charged area would be quite unaffected. Therefore, the calculated charge interactions while very low in level, are nonetheless valid. We are theoretically at liberty to specify the circumstances for which we choose to calculate the local effects of one electric charge on another, one magnetic field on another, or a magnetic potential on a gravitational potential (both being manifestations of inertial equivalence) thereby choosing the appropriate "gauge". Two features of the universe take care of the independence of any small piece of it: first, the conservation of electric charge; secondly, the ability of electric charges in different parts of the universe to communicate with one another.

The external magnetic field produced by the action potential of a frog's sciatic nerve has been measured at $1.2 \times 10^{-10}$ tesla at 1.3 mm from the nerve, with a signal to noise ratio of 40 to 1. Modeling this field at a change in potential on the order of 70 mV, a peak current is estimated at 5–10 microamperes. Similarly, when a comparable field is produced by driving the solenoid of the present invention, a current amplitude of about $10^{-5}$ amps is produced in a conductor approximating the length of the frog, which demonstrates the congruence of equating gravitational and quantum energies. Therefore, weak physiologic magnetic fields, both steady state and alternating in polarity, the fields being on the order of $10^{-8}$ gauss in humans, are maintained in accordance with particular endogenous and exogenous fields and current densities and potential gradience on the order of a micoramp.

Amplitude modulated (alternating) magnetic resonance may be indicated. In that case the mass of the etiological genetic quantum character is used in $mc^2 = $ BvL coulomb to determine the value of B. Once the correct amplitude is derived, then the cyclotron resonance equation is used:

$$fc = \frac{e^- B}{2\pi m},$$

$10^{-19}$ coulombs (the charge of a single electron), B = physiologic flux density required for adjustment to health derived by $mc^2 = $ BvL coulomb, $\pi = 3.1416$, $m = 9.11 \times 10^{-28}$ grams (the electron's mass); this will determine the necessary frequency of the applied therapeutic electromagnetic signal. Since the gyromagnetic ratio of the electron remains constant, according to the quantum Hall effect, the relation of the D-C magnetic field associated with delta brain waves (which has been measured to be about $5 \times 10^{-8}$ gauss) to the necessary frequency of the therapeutic signal, may be as follows:

$$fc \text{ (72 beats/minute)} = \frac{1.6 \times 10^{-19} \text{ coul} \times 4.3 \times 10^{-8} \text{ gauss}}{2\pi \times 9.11 \times 10^{-28} \text{ grams}}$$

(Normal heart rate is related to brain's D-C magnetic field.)

Using silicon wire, for example, this field may be created by the following solenoidal system:

$$B \text{ (4.3} \times 10^{-8} \text{ gauss)} = H_2O \text{ (10.3)} \cdot \frac{N(13) \cdot I(10^{-7} \text{ amperes})}{\text{Length (300 cm)}}$$

It has been demonstrated in clinical studies that exogenously administered electromagnetic fields can induce increased transcription (RNA synthesis) and translation (protein synthesis). Alterations in electrical fields of a biological element such as a gene or the like, are considered to be directly affected by and related to function and metabolic rate in adjacent biological elements. Accordingly, a stable healthy condition of homeostasis is achieved in a healthy physiology, while with deterioration of homeostasis, the physiology and metabolism will deteriorate rapidly.

It has been shown that D-C current or alternating current in bones will produce osteochondrogenesis and bacteriostasis and will affect ATP generation, protein synthesis and membrane transport. Membrane transport systems are thought to be of a cyclotron resonance quality, in that magnetic fields turn an ion in a channel (of Heisenberg uncertainty) and frequency accelerates it through the membrane which regulates endogenous ion flux. A-C fields and D-C fields are of course associated with alterations of atoms in space via electromagnetic fields, including manipulation in the dipteran. This shows on a cellular level the mechanical vibration alterations in RNA and proteins from electrical oscillations exogenously produced. Electrical fields inside the nucleus are changed by exogenously applied electromagnetic fields, so that DNA synthesis is increased in human fibroblasts when electromagnetic fields, in the form of sinusoidal waves between 15 and 4000 Hertz, are changed into mechanical or structural alterations representing deformation of atomic lattices by some free movement of electrons. Accordingly, biochemical covalent bonds and lattices can be considered piezoelectric as well as electrostatic operating devices.

The quality of the gene as a piezoelectric substance must be analyzed, because then NMR and ESR clarify as manifestations of the phenomenon of magnetic resonance to permeate all matter, especially including DNA, RNA, protein regulators, growth hormones and enzymes. Thus the human body becomes a straight conductor "1" most particularly a semi-conductor, which when placed in water to improved conductivity is functionally effected by electromagnetic fields as low as $10^{-8}$ gauss, applied externally at right angles to the patient's length.

Oncogenes (Cancer activatable genes) abound in brain and glial cells, and have been incriminated as anti-regenerative agents. Similarly, viral genes responsible for oncogenic transformation are derived from normal vertebrate genes. Therefore, molecular biologists must accept that these normal cellular "oncogenes" are important regulators of cell growth and differention.

Mutation rate of cells, cell growth, the length of plasmids in bacteria exposed to applied electromagnetic fields, DNA synthesis, transcription and translation in cells, and repair, are all parameters by which to measure the relevance of magneto-therapy on a fundamental level.

On a fundamental level, electron spin precession and spin axes are reorientated in space by the vibration of the fundamental particles comprising the metric itself of space-time. Even photons, a form of carrier of EM force, change orientation in space through resonance vibrations bringing about electron spin resonance and proton spin resonance or NMR. Induced reorientation of atomic magnetic moments, of atomic structural and magnetic domains, reorientate submolecular and molecular magnetic domains. Said reorientation of molecular domains brings about "jumping" of atoms from one place to another, instantaneously, according to Heisenberg uncertainty. Ion fluxes in membrane channels are just a spontaneously reorientated in accord with multiple cyclotron resonance models, allowing models of particular structures, wherein the charge density is greatest in the middle, and whose sides change potential in a synchronous fashion. This means that an oncogene, which is just a little different from a normal gene, can be induced electromagnetically into an altered structural state, if an oncogene is a piezoelectric substance.

As a second effect on a basic level, the Hall effect is another mechanism besides the piezoelectric nature of DNA, which of course regulates metabolism. The current carrying conductor, in this case the human organism, when placed in a magnetic field will have a small EMF induced cross-sectionally in a magnetic field. When the Hall effect induced voltage is equaled by a transverse current density, a certain current is set up in the human, achieving a physiologic balance. The force is generated lengthwise as the human travels with the earth at a velocity of $3 \times 10^6$ cm/s, and additionally carried as a charge in coil about the earth's axis of rotation, cutting lines of force at right angles to the angular velocity.

It has been determined that a pulsing electromagnetic field in clinical use induces an electric field of about 1 mV/cm in the extra cellular fluid, translating into a current on the order of a few microamperes per square centimeter. The result is a human physiological magnetic field on the order of $10^{-8}$ gauss, across a semi-conductor of several feet in length.

There is angular momentum associated with each motion of an electron, and the earth, which is a total of orbital and spin angular momentum. If we were to model the electron as a single point, no angular momentum would be possible. We may choose to model all particles as points which actually have geometricity lending to the concept of string, or an extension of such points through space-time. The electron may be modeled as a spinning sphere. Because the sphere carries an electric charge when the particle is an electron, the spinning motion leads to current loops and to a magnetic moment, when the magnetic moment is defined as the charge to mass ratio of an electron times the spin angular momentum. Magnetic moment is an inertial frame of momentum, of energy as matter moves. If this magnetic moment really exists and regulates the energy levels of the atom, and the wave lengths of spectral lines, then when an atom, or any object whatsoever, is placed in a magnetic field, there is an interaction with the field. And, indeed, associated with this interaction is a potential energy, pointing to the gravitational potential. Such shifts are indeed observed in precise spectroscopic analysis. As the potential energy of a body changes the concomitant kinetic change moves the object through space. This movement is subject to Heisenberg's probability principle. One cannot know precisely where an object is and what velocity it has, simultaneously.

Evidence has shown conclusively that the electron does have angular momentum and magnetic moment that are not related to the orbital motion but are intrinsic to the particle itself. Spin angular momentum is quantized.

As photons carry the force of electromagnetism one may not directly observe the structure of an atom. But the limitations our universe sets for us are infinite by definition according to Einstein as he preferred to say "We cannot ever measure the radius of the universe by time". This is the second postulate of General Relativity. The first postulate was basically a representation of space as having a average density everywhere the same and different from zero. The concept of quantum gravity indicates the possibility of all ponderable bodies of field to exist in point-mass potential comprising the metric of space-time itself. We then compare our earth to an electron conceptually. An oncogene is merely an aggregate of atoms, the integrated vector sum of which has a quantized magnetic moment on a level of structure and function in which the oncogene is a point-mass instead of an electron. A volume containing domains of atoms would have a potential intrinsic to itself in a space-time continuum.

Atoms jump in space, genes jump in space, molecules jump in space, as electrons jump in space. Herein is the fundamental notion from which clinical significance of the present invention is derived. According to the invention, atoms of oncogenes can be directed to jump into spaces which create a normal homologous gene by the action of applied electromagnetic fields, in resonance with the stiffness of the system associated with the oncogene. The vibration of the system by a certain magnitude of force may be attuned to the vibrating system of only structures of the mass of an oncogene. Atoms of an oncogene electromagnetically misaligned can be ordered to fall into place like iron filings around a magnet. Accordingly, the harmony of life can be considered to be ordered electromagnetically and can be re-ordered in this way.

Symmetries of relative point masses may be expressed by equivalent ratios in nature, including the ratio of a photon's mass to an oncogene's mass ($8 \times 10^{-43}$ grams/$1.6 \times 10^{-19}$ grams), which is equal to the ratio of the average circulating immunoglobulin mass to human mass, (i.e., $1.6 \times 10^{-19}$ grams/$3 \times 10^4$ grams). Similarly, the same ratio is found in the human mass to the earth's mass, ($3 \times 10^4$ grams/ $6 \times 10^{27}$ grams). The foregoing is for a small human (66 lbs.) and the photon at $f=10^5$. One can also compare with the same success the ratio of photon mass at $f=10^4$ to the gene mass and circulating immunoglobulin mass ($7 \times 10^{-42}$ gram/ $7 \times 10^{-19}$ gram) to the ratio of a normal human mass to the earth's mass, ($6 \times 10^4$ (132 lbs.)/ $6 \times 10^{27}$ grams). This ratio is equal to the ratio of the gene or immunoglobulin mass to the human mass ($7 \times 10^{-19}$ grams/$6 \times 10^4$ grams (132 lbs.). In each case, the resultant quotient is about $10^{-24}$, which is the mass in grams of a baryon (proton). The mass of the photon at $8 \times 10^{-43}$ grams is about equal to the number of the Planck time, and $1.6 \times 10^{-19}$ is the number for the charge of an electron, in coulombs, exactly the same as the average number in grams for the mass of a circulating immunoglobulin. The symmetries demonstrate a relationship which the invention draws upon.

As a conclusion, very positive therapeutic results will be achieved from utilizing physiological magnetic fields the order of $10^{-8}$ gauss, approximately the same number as Newton's Gravitational Constant in cgs, applied to a patient within a solenoid immersed in water. Amplitude modulated resonance may be achieved allowing manipulation of oncogenes, viral nucleic acids and growth factors with magneto-therapy. The same process can be extended to treat terminal cancer patients, and victims of AIDS, genetic disorders like MD and CNS regeneration. The common denominator is subatomic and the interaction initiated instantly, everywhere.

Specific calculations according to the foregoing procedure are approximately processed based on the mass of the target. A light rope of m-RNA of molecular weight 23 kilodaltons, or $4 \times 10^{-20}$ grams is set in dual resonance with a physiologic magnetic field produced by an outside impressed electromagnetic field comparable to endogenously sourced electromagnetic signals which reorient the spin angular momentum of electrons, the physiologic magnetic domains being directly dependent upon the invariance of the electron's gyromagnetic ratio. The field will readjust crystal atomic lattice structures inducing recrystallizations and translocations of the targets to produce homologous structures and equilibrium of charge distribution. Targets from cancer and degenerative disorders of the PNS and CNS include the following examples:

Crystal single angular light polypeptide chains and dimers of light chains (approximately 7–70 kilodaltons) i.e., the class of monoclonal immunoglobulins, immunogens and dimers thereof, various growth factors, and light ropes of m-RNA are distinctive relatives of, regulators and regulated by, brainwaves, most notably delta and theta brainwaves.

Immunogenic, pathogenic magnetic domains, or genomic magnetic domains as well as domains wherein deletions produce pathogenetic processes are related to brainwaves, most notably alpha and beta brainwaves. Light genomic domain segments, e.g., from about 7 kilodaltons to 70,000 kilodaltons can be examined for potential oncogenicity. Oncogenes have generally been considered to be of the magnitude 250–1,000 base pairs. Generally, molecular weights of over 100 kilodaltons have been clinically demonstrated to be related to the foregoing pathogenic manifestations. Gene defects as in the X chromosome, specifically the short arm, as in MD, show deletions rather than substitutions over an extended genomic chain of length greater than 1,000 bases. The lack of dystrophin, a 300,000 dalton protein is the result in evidence. Applying the ranges of proposed magnetic fields for clinical use as propitiators of recrystallization of misaligned subatomic and molecular magnetic domains, the following frequencies and flux densities can be calculated. Pertinent approximate ranges of flux densities and cyclotron resonance frequencies are given for treatment of cancer with magnetotherapy by the following calculations:

$$mc^2 = Bvl \text{ coulomb}$$

mass * $9 \times 10^{20}$ cm$^2$/s$^2$ = flux density * earth orbital velocity * average adult height mass * $9 \times 10^{20}$ = B * $3 \times 10^6$ cm/s * $1.7 \times 10^2$ cm.

Solved for seven kilodaltons, the minimum mass of an oncogene associated protein, a flux density B of $2.1 \times 10^{-8}$ gauss results.

Further applying the foregoing constant to the cyclotron resonance equation, $f_c = (e^{-*} B)/(2\pi m) = (1.6 \times 10^{-19}$ coulombs * B$)/(6.28 \times 9.11 \times 10^{-28}$ g$)$. The ratio of the electron charge to mass is invariant.

$$f_c = 2.79874 \times 10^7 \text{ coulomb/gram} * 2.1 \times 10^{-8} \text{ gauss.}$$

Therefore, $f_c$ is approximately equal to 0.6 Hertz, or 35 cycles per minute.

According to the foregoing, a minimum therapeutic signal for cancer would yield a flux density of $2.1 \times 10^{-8}$ gauss with a frequency of about 0.6 Hertz, for comparatively light proteins which are associated with oncogenes. Polypeptide chains on the order of 10 kilodaltons to about 40 kilodaltons, which are associated with delta brainwaves, are of the same range as other pertinent molecules such as NGF, EGF, PDGF. Oncogenes associated proteins such as trophic factors are important targets in cancer as they may lock in the "on" position and over produce trophic factors resulting in neoplasia; and they are the pertinent targets to attack degenerative disorders of the PNS and CNS.

One can solve for the molecular of the adenine nucleotide (267.176 daltons), guanine (299.176), cytosine (243.152), thymine (258.164) and uracil (261.144).

Solving the subject equation where m = 13,250 daltons, the mass of a single protein of two identical proteins that comprise the NGF molecule, the flux density B of $3.9 \times 10^{-8}$ gauss results. Similarly, the resonance frequency $f_c = 1.09$ Hertz or 65.4 beats per minute.

Note the fundamental correlation of NGF to delta brain wave frequency, while keeping in mind that CNS and PNS nerve cells that have been demonstrated to respond to NGF include the sensory and sympathetic which regulate involuntary functions such as the beating of the heart and blood flow. In the periphery NGF acts in sympathetic neurons that use catecholamine neurotransmitters such as norepi and dopamine on sensory nerve cells that make certain neuroactive peptides. In the brain NGF acts in neurons that use the neurotransmitter acetylcholine. The brain tracks that respond to NGF include those that degenerate in Alzheimer's and Huntington's disease. This raises the possibility that the failure to produce or respond to NGF might contribute to the development of these serious neurological disorders. Indeed, the atomic crystal lattice structure of the NGF molecule may prove a pertinent factor; as well as the structural disposition of the genomic magnetic domain related to the production or lack thereof of the trophic factor. Herein we view the NGF molecule and its genomic relatives important foci in the approach to cancer, heart disease, PNS and CNS regeneration. Additionally, it may be that NGF is a vital trophic factor with respect to development and maintenance of the integrity of such vital structures as the optic and auditory nerves.

$$f_c = \frac{1.6 \times 10^{-19} \text{ coul} \cdot 3.9 \times 10^{-8} \text{ gauss}}{(6.28) 1.67 \times 10^{-24} \text{ g}}$$

(wherein B=NGF associated flux density and the ion is the proton)

$$f_c = 5.95 \times 10^{-4} \text{ Hz}$$

We see the source of the relativistic unchanging physiologic magnetic field in the BCEC (biologically closed electric circuit); and the vital importance of blood pH stability.

$$2.213 \times 10^{-20} \text{ g} \cdot 9 \times 10^{20} \frac{\text{cm}^2}{\text{s}^2} =$$
(NGF)

$$B \cdot 3 \times 10^6 \frac{\text{cm}}{\text{s}} \cdot 0.56 \times 10^2 \text{ cm}$$
(newborn's length)

(wherein m = 13.25 kilodaltons and 1 = infant's length)
$B = 1.1855 \times 10^{-7}$ gauss $$f_c = 2.79874 \times 10^7 \frac{\text{coul}}{\text{g}} \cdot 1.1855 \times 10^{-7} \text{ gauss}$$

$$f_c = 3.3179 \text{ Hz (199 beats/min)}$$

Herein we note the criticality of the NGF mass in the determination of resting (delta) brain waves in the infant as well as the adult. Clearly, adjustments in the adult include the relation of dimers of light protein chains (42 kilodaltons) delta waves. Additionally we should note that DC fields produced and maintained by protons and larger ions serve to stabilize heart rate, i.e., reduce the frequency created by NGF interaction thereby moderating the physiological mechanism. Thus we conclude that although NGF is critically important to the maintenance of physiological magnetic fields, it is not a singular regulatory factor. It may, however, prove to be the most important single regulatory factor, as we see the reason that nature presents us with an NGF molecule of molecular weight 26.5 kilodaltons, comprised of two identical protein chains each having a mass of 13.25 kilodaltons.

$$3.5 \times 10^{-20} \text{ g} \cdot 9 \times 10^{20} \frac{\text{cm}^2}{\text{s}^2} = B \cdot 3 \times 10^6 \frac{\text{cm}}{\text{s}} \cdot 1.7 \times 10^2 \text{ cm}$$
(oncogene associated protein; bladder carcinoma)
(wherein m = 21 kilodaltons, light chain m-RNA; HTLVI virus (TAT O leukemia oncogene associated protein at 17 kilodaltons)
$B = 6.1765 \times 10^{-8}$ gauss $$f_c = 2.79874 \times 10^7 \frac{\text{coul}}{\text{g}} \cdot (6.1765 \times 10^{-8} \text{ gauss})$$

-continued
$$f_c = 1.7286335 \text{ Hz (103.7 beats/min delta frequency)}$$

$$4.4255 \cdot 10^{-20} \text{ g} \cdot 9 \times 19^{20} \frac{\text{cm}^2}{\text{s}^2} = B \cdot 3 \times 10^6 \frac{\text{cm}}{\text{s}} \cdot 1.7 \times 10^2 \text{ cm}$$
(NGF molecule)

$$B = 7.8097 \times 10^{-8} \text{ gauss}$$

$$f_c = 2.79874 \times 10^7 \frac{\text{coul}}{\text{g}} \cdot 7.8097 \times 10^{-8} \text{ gauss}$$

$$f_c = 2.185732 \text{ Hz (131.144 beats/min)}$$

$$5.01 \times 10^{-20} \text{ g} \cdot 9 \times 10^{20} \frac{\text{cm}^2}{\text{s}^2} =$$

$$B \cdot 3 \times 10^6 \frac{\text{cm}}{\text{s}} \cdot 1.7 \times 10^2 \text{ cm}$$

(30 kilodaltons PDGF onc-associated proein:osteosarcoma)

$$B = 8.84 \times 10^{-8} \text{ gauss}$$

$$f_c = 2.79874 \times 10^7 \frac{\text{coul}}{\text{g}} \cdot 8.84 \times 10^{-8} \text{ gauss}$$

$$f_c = 2.4740861 \text{ Hz (148.44 beats/min delta frequency)}$$

$$7.01 \times 10^{-20} \text{ g} \cdot 9 \times 10^{20} \frac{\text{cm}^2}{\text{s}^2} =$$

$$B \cdot B \times 10^6 \frac{\text{cm}}{\text{s}} \cdot 1.7 \times 10^2 \text{ cm}$$

(42 kilodaltons
BJP - wherein m = 42 kilodaltons, BJP — Bence Jones Protein, dimers of light chains, genomic magnetic domains associated with EGF having 53 amino acids; the average mass of the genomic nucleotide for approximation purposes is 267 kilodaltons, note each triplet codon encodes 1 amino acid)

$$B = 1.237 \times 10^{-7} \text{ gauss}$$

$$f_c = 2.79874 \times 10^7 \frac{\text{coul}}{\text{g}} \cdot 1.237 \times 10^{-10} \text{ gauss}$$

$$f_c = 3.462 \text{ Hz (207.7 beats/min, note maximum delta frequency)}$$

$$1.002 \times 10^{-19} \text{ g} \cdot 9 \times 10^{20} \frac{\text{cm}^2}{\text{s}^2} =$$

$$B \cdot 3 \times 10^6 \frac{\text{cm}}{\text{s}} \cdot 1.7 \times 10^2 \text{ cm}$$

(60 kilodaltons; skeletal growth factor pp60 wherein m = 60 kilodaltons, the mass of pp60 an important neuronal factor)

$$B = 1.7647 \times 10^{-7} \text{ gauss}$$

$$f_c = 2.79874 \times 10^7 \frac{\text{coul}}{\text{g}} \cdot 1.7647 \times 10^{-7} \text{ gauss}$$

$$f_c = 4.9389 \text{ Hz (296 beats/min, theta frequency, transitional)}$$

$$1.356 \times 10^{-19} \text{ g} \cdot 9 \times 10^{20} \frac{\text{cm}^2}{\text{s}^2} =$$

$$B \cdot 3 \times 10^6 \frac{\text{cm}}{\text{s}} \cdot 1.7 \times 10^2 \text{ cm}$$

(68 kilodaltons
wherein m = 68 kilodaltons, the mass of Hb, a relative maximum for onc-associated proteins, genomic magnetic domain of 255 nucleotides)

$$B = 2.004 \times 10^{-7} \text{ gauss}$$

$$f_c = 2.79874 \times 10^7 \frac{\text{coul}}{\text{g}} \cdot 2.004 \times 10^{-7} \text{ gauss}$$

-continued $f_c = 5.60867$ Hz (336.5 beats/min theta frequency)

$$1.67 \times 10^{-19} \text{ g} \cdot 9 \times 10^{20} \frac{\text{cm}^2}{\text{s}} = B \cdot 3 \times 10^6 \frac{\text{cm}}{\text{s}} \cdot 1.7 \times 10^2 \text{ cm}$$

(100 kilodaltons,
same number as q of e⁻ in grams average circulating immunoglobulin, minimum oncogene rope)
(wherein m = 100 kilodaltons, the average mass of a circulating immunoglobulin, 375 nucleotide chain magnetic domain, a single rope of a minimum sized oncogene which is generally 350 base pairs, genomic magnetic domain associated with 118 amino acid sub-unit protein chain of NGF)

$$B = 2.947 \times 10^{-7} \text{ gauss}$$

$$f_c = 2.79874 \times 10^7 \frac{\text{coul}}{\text{g}} \cdot 2.947 \times 10^{-7} \text{ gauss}$$

$f_c = 8.248$ Hz (minimum alpha wave frequency)
critical transitional target mass 495 beats/min $$4.4589 \times 10^{-19} \text{ g} \cdot 9 \times 10^{20} \frac{\text{cm}^2}{\text{s}^2} =$$
$$B \cdot 3 \times 10^6 \frac{\text{cm}}{\text{s}} \cdot 1.7 \times 10^2 \text{ cm}$$

(1,000 kilodaltons,
wherein m = 1,000 kilodaltons, the relative maximum oncogene magnetic domain, single rope)

$$B = 7.868 \times 10^{-7} \text{ gauss}$$

$$f_c = 2.79874 \times 10^7 \frac{\text{coul}}{\text{g}} \cdot 7.868 \times 10^{-7} \text{ gauss}$$

$f_c = 22$ Hz (beta frequency)

Therefore a 590 base rope is a critical transitional magnetic domain mass because alpha waves usually range in frequency from 8–13 Hz. Dystrophin, a 300 kilodalton protein, is perhaps a critical mass protein related to important immunogenic, genomic magnetic domain size. This is not to say, however, that larger genomic magnetic domains will not prove to be important targets, indeed it is estimated that targets ranging up to 3 million daltons will prove efficacious in the treatment of various viral disorders such as AIDS.

The following table illustrates further target masses appropriate for treatment according to the invention.

| Targets | Molecular Weight (m) | Flux density (B) | Frequency ($f_c$) |
|---|---|---|---|
| whole virus (HIV) | (5 unique genes and structural proteins) + 9,000 base pairs (genome) = 2.43 × 10⁶ daltons (4 × 10⁻¹⁸ g) | 7.0588 × 10⁻⁶ gauss<br>8.8235 × 10⁻⁶ gauss | 197.55745 Hz<br>246.9468 Hz |
| envelope protein | 120 kilodaltons (2 × 10⁻¹⁹ g) | 3.529 × 10⁻⁷ gauss | 9.87675 Hz (apha) |
| envelope protein | 41 kilodaltons (6.85 × 10⁻²⁰ g) | 1.2088 × 10⁻⁷ gauss | 3.38312 Hz (delta) |
| capsid protein | 24 kilodaltons (4 × 10⁻²⁰ g) | 7.0588 × 10⁻⁸ gauss | 1.975575 Hz (delta) |
| capsid protein | 55 kilodaltons (9 × 185 × 10⁻²⁰ g) | 1.62088 × 10⁻⁷ gauss | 4.53642 Hz (theta) |
| reverse transcription enzyme | 65 kilodaltons (1.0855 × 10⁻¹⁹ g) | 1.91559 × 10⁻⁷ gauss | 5.361238 Hz (theta) |

POTENTIAL TARGETS AND MAGNETO-THERAPY PARAMETERS IN AIDS

The level of current inducted via magnetic field generated by a solenoid can also be applied by other methods. The required current can be generated by applying electrodes directly to the patient, or by applying plates connected to a source of electric potential sufficient to produce the required current.

The present calculations for selecting a precisely appropriate field strength for therapeutic application of energy to mammals, also operate for non-mammals. Beneficial effects can be achieved as to any animal, plant, microbe or the like, which are controlled or affected by the genetic materials subject to treatment.

It should be understood that the foregoing is illustrative of the instant invention and should not be considered limitative or restrictive thereof. The scope of the invention may be further described within the scope of the attached claims.

I claim:

1. A method for therapeutically treating patients suffering from disease conditions, comprising:
   calculating an electromagnetic field by equating a gravitational energy of a target element with the energy per unit charge of an electromagnetic field induced therein, using the formula mc²=Bvl coulomb, thereby deriving a magnetic flux density of between about 6×10⁻⁶ to 6×10⁻¹⁰ gauss; and
   subjecting said patients over an extended period of time to an electromagnetic field at said flux density.

2. The method of claim 1, wherein the magnetic field is applied using a solenoid to which electric power has been applied.

3. The method of claim 2, wherein the voltage applied to the solenoid is between about 0.1 and about 7.5 volt.

4. The method of claim 1, wherein the patient is aligned at right angles to the electromagnetic field.

5. The method of claim 1, wherein the desired flux density is calculated according to said equation by letting m=the mass of a quantum genetic target character, c=the velocity of light, v=the orbital velocity of the earth and l =the height of the patient.

6. The method of claim 5, further comprising calculating an alternating field frequency for said electromagnetic field, by operating the field at a frequency $f_c=(e^-B)/2\pi$ m, where $f_c$ equals cycles per second or Hertz; e⁻=1.6×10⁻¹⁹ coulombs (the charge of an electron); B=the physiologic flux density as calculated according to said method; and, m =9.11×10⁻²⁸ grams (the mass of an electron).

7. A method for therapeutically treating patients suffering from central nervous system degeneration, comprising:
   calculating an electromagnetic field by equating a gravitational energy of a target element with the energy per unit charge of an electromagnetic field induced therein, using the formula mc²=Bvl coulomb, thereby deriving a magnetic flux density of between about 6×10⁻⁶ to 6×10⁻¹⁰ gauss; and
   subjecting said patients over an extended period of time to an electromagnetic field at said flux density.

8. The method of claim 7, wherein the magnetic field is applied using a solenoid to which electric power has been applied.

9. The method of claim 8, wherein the voltage applied to the solenoid is between about 0.1 and about 7.5 volt.

10. The method of claim 7, wherein the patient is aligned at right angles to the electromagnetic field.

11. The method of claim 7, wherein the desired flux density is calculated according to said equation by letting m=the mass of a quantum genetic target character, c=the velocity of light, v=the orbital velocity of the earth and l=the height of the patient.

12. The method of claim 11, further comprising calculating an alternating field frequency for said electromagnetic field, by operating the field at a frequency $f_c = (e^- B)/2\pi$ m, where $f_c$ equals cycles per second or Hertz; $e^- = 1.6 \times 10^{-19}$ coulombs (the charge of an electron); B=the physiologic flux density as calculated according to said method; and, $m = 9.11 \times 10^{-28}$ grams (the mass of an electron).

* * * * *